United States Patent
Allegrini et al.

(10) Patent No.: US 7,164,029 B2
(45) Date of Patent: Jan. 16, 2007

(54) PROCESS FOR THE PREPARATION OF BENZYLIMIDAZOLE DERIVATIVES

(75) Inventors: Pietro Allegrini, San Donato Milanese (IT); Gabriele Razzetti, Sesto S. Giovanni (IT); Graziano Castaldi, Briona (IT); Vittorio Lucchini, S. Donato Milanese (IT)

(73) Assignee: Dipharma S.p.A., Mereto Di Tomba (IT)

( * ) Notice: Subject to any disclaimer, the term of this patent is extended or adjusted under 35 U.S.C. 154(b) by 131 days.

(21) Appl. No.: 10/969,354

(22) Filed: Oct. 21, 2004

(65) Prior Publication Data

US 2005/0090672 A1    Apr. 28, 2005

(30) Foreign Application Priority Data

Oct. 23, 2003   (IT) .......................... MI2003A2069

(51) Int. Cl.
  *C07D 233/68*   (2006.01)
  *C07D 233/70*   (2006.01)

(52) U.S. Cl. ................................. 548/341.1; 548/316.4

(58) Field of Classification Search ............ 548/341.1, 548/316.4; 564/164

See application file for complete search history.

(56) References Cited

FOREIGN PATENT DOCUMENTS

WO     WO 2003084959 A1 * 10/2003

OTHER PUBLICATIONS

Larsen et al. J. Org. Chem. 1994, 59, 6391-6394.*

* cited by examiner

*Primary Examiner*—Joseph K. McKane
*Assistant Examiner*—Jason M. Nolan
(74) *Attorney, Agent, or Firm*—Young & Thompson

(57) ABSTRACT

A process for the preparation of benzylimidazole derivatives useful as intermediates for preparation of losartan, novel intermediates for their preparation and a process for the preparation of losartan.

10 Claims, No Drawings

PROCESS FOR THE PREPARATION OF BENZYLIMIDAZOLE DERIVATIVES

FIELD OF THE INVENTION

The present invention relates to a novel process for the preparation of benzylimidazole derivatives useful for the preparation of losartan, novel intermediates for their preparation and a process for the preparation of losartan using said derivatives.

BACKGROUND OF THE INVENTION

Losartan potassium, i.e. 2-n-butyl-4-chloro-1-[(2'-(tetrazol-5-yl)-1,1'-biphenyl-4-il)methyl]-1H-imidazole-5-methanol potassium salt, is a known angiotensin II antagonist widely used in therapy, for example in the treatment of hypertension, having the following formula (I)

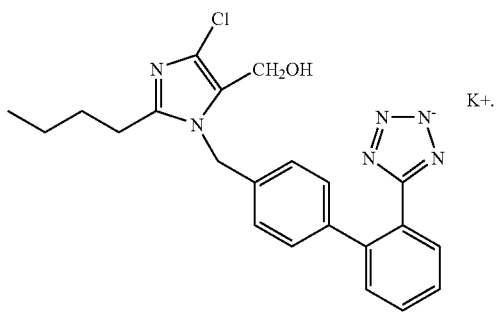

According to one of the various known synthetic routes for the preparation of losartan, one of the key intermediates is 1-bromo-4-(2'-butyl4'-chloro-5-hydroxymethylimidazole-1'H-1'-yl) methylbenzene, having the formula c) reported below. The preparation of this intermediate disclosed in WO 93/10106 comprises the reaction between 2-n-butyl-4-chloro-1-H-indazole-5-carboxaldehyde of formula a) and p-bromo-benzyl bromide of formula b) to give the compound of formula c).

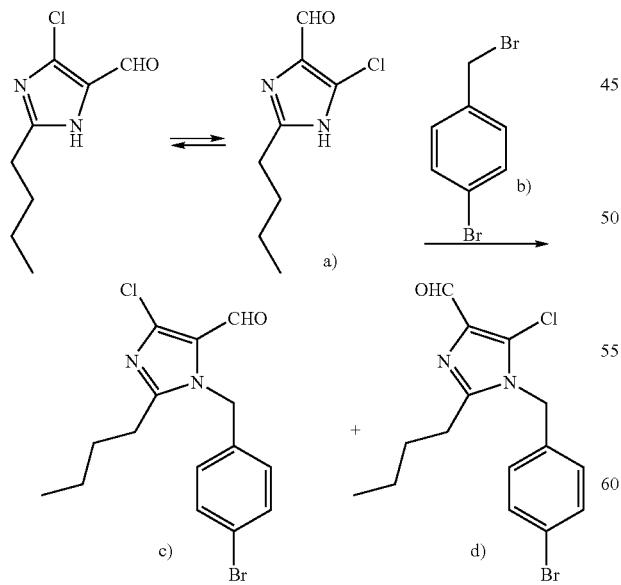

This method is not selective, due to the fact that the imidazole compound of formula a) exists in 2 tautomeric forms which both react with the compound of formula b) leading to the formation of the desired compound of formula c) and of its position isomer of formula d). Since the compound of formula d) has a chemical behaviour similar to the compound of formula c), in the cross-coupling reactions that lead to the formation of losartan potassium, it gives rise to an impurity which can be removed only by means of repeated and troublesome crystallizations, which significantly decrease the yield and increase production costs.

There is therefore the need for a new method for preparing the said benzylimidazole intermediate which overcomes the aforementioned drawbacks.

DESCRIPTION OF THE INVENTION

In a first embodiment, the present invention relates to a novel process for the preparation of compounds having the following formula (II)

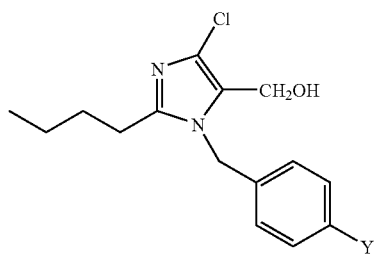

wherein Y is a leaving group,
the process comprising:
chloroformylation of a compound of formula (III)

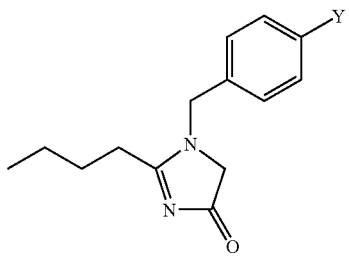

wherein Y is as defined above,
to obtain a compound of formula (IV)

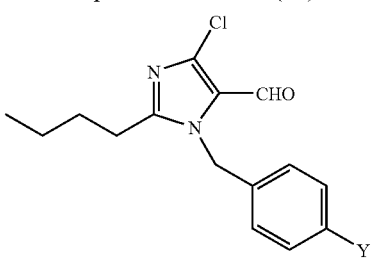

wherein Y is as defined above,
and reduction of the aldehyde group to alcohol.

The leaving group Y is for example a halogen atom, preferably chlorine or bromine, in particular bromine, or a hydroxy group activated to esterification, for example through an alkylsulfonyl group, typically mesylate, or an arylsulfonyl group, typically tosylate, or a perfluoroalkylsulfonyl group, for example trifluoromethanesulfonyl and nonafluorobutanesulfonyl.

The chloroformilation reaction can be carried out for example by treatment of a compound of formula (III) first with phosphorous oxychloride and then with dimethylformamide (DMF). The chlorination phase is carried out by treatment with phosphorous oxychloride in a molar ratio from 2 to 4, preferably 3, with the compound of formula (III), the addition being carried out at a temperature ranging from −10 to 10° C., preferably at about 5° C., followed by heating at about 90° C. for a time ranging from 30 min. to 2 hours. In the subsequent step, DMF is added at about 90° C., in a stoichiometric ratio from 2 to 4 equivalents, preferably 3, and the reaction is refluxed for 3–5 hours. The solvent is typically an inert organic solvent, for example toluene or xylene, preferably toluene.

Alternatively, the reaction can be carried out by treatment of a compound of formula (III) with a suitable N,N-dimethylformamide dialkylacetal, for example N,N-dimethylformamide dimethylacetal, N,N-dimethylformamide diisopropylacetal or N,N-dimethylformamide diisobutylacetal, preferably N,N-dimethylformamide dimethylacetal, followed by treatment with phosphorous oxychloride. The reaction is typically carried out in a inert organic solvent, for example toluene or xylene, preferably toluene. The formylation reaction is carried out at a temperature ranging from −50 to 100° C. and the chlorination reaction is carried out at a temperature ranging from 50 to 150° C.

The reduction of the aldehyde group to alcohol to give a compound of formula (IV) can be performed with known methods, for example by treatment with an alkali metal borohydride, preferably sodium borohydride or potassium borohydride, or with tetramethylammonium borohydride, in a molar ratio from about 0.25 to 2, preferably 1. The reaction is performed at a temperature ranging from −30 to 50° C., preferably from 0 to 5° C. Suitable solvents are for example alcohols, preferably methanol, ethanol, isopropanol and butanol; or aromatic hydrocarbons, for example toluene, halogenated hydrocarbons, for example methylene chloride; or esters, preferably ethyl acetate, isopropyl acetate or butyl acetate; or ethers, preferably tetrahydrofuran or dioxane, in mixtures with water and optionally in the presence of a phase transfer catalyst, for example tetraalkylammonium halides or hydrosulfates.

The compounds of formula (III) are novel and are a further object of the invention.

A compound of formula (III) can be obtained by reaction of a compound of formula (V)

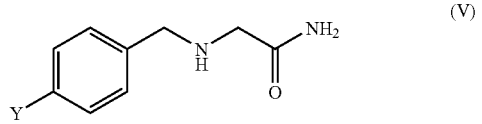

wherein Y is as defined above,
with a trialkyl orthovalerate, for example a tri-($C_1$–$C_6$) alkyl orthovalerate, preferably trimethyl valerate.

The reaction of the compound of formula (V) with the trialkyl orthovalerate, typically trimethyl orthovalerate, is carried out using a stoichiometric ratio between the compound of formula (V) and the trialkyl orthovalerate from 1/1 to 1/1.5, preferably 1/1.2. The reaction is carried out in the presence of catalytic amounts of an acid ranging from 1 to 10% molar, preferably about 5%. Said acid can be a mineral acid, for example sulfuric acid, or an organic acid, for example formic, acetic, methanesulfonic or camphorsulfonic acid, preferably acetic acid. The reaction temperature ranges from about 65 to 120° C., preferably from 80 to 110° C., so as to remove the methanol that forms. The reaction can be performed in the absence of solvents, or in an organic solvent, for example a hydrocarbon, preferably toluene, or a high-boiling chloride, preferably dichloroethane. The resulting compound of formula (III) is subjected chloroformylation, preferably without being recovered from the reaction mixture.

The compound of formula (V) wherein Y is chlorine is known, for example, from J. Am. Chem. Soc., (1956), 78, 6189–92. The compounds of formula (V) wherein Y, being as defined above, is other than chlorine are novel and are a further object of the invention. The compounds of formula (V) can be obtained according to known methods, for example by reductive amination, as shown in the following scheme.

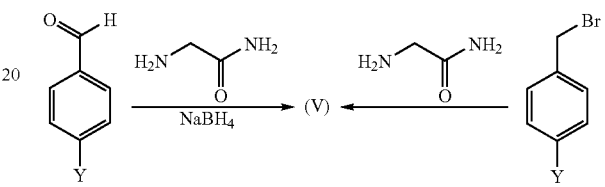

The present invention relates also to a novel method for the preparation of losartan, or a pharmaceutically acceptable salt thereof, in particular the potassium salt, comprising:
reaction of a compound of formula (II), as defined above, with a synthon of formula (VI)

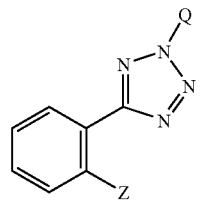

wherein Q is a tetrazole protecting group; and Z is a —B($R_1R_2$) group wherein each of $R_1$ and $R_2$, which can be the same or different, is halogen, hydroxy or $C_1$–$C_4$ alkoxy; or Z is a lithium or copper atom, or a halogenated metal;
removal of the protecting group Q; and, if desired,
conversion of losartan in a pharmaceutically acceptable salt thereof; characterised in that the compound of formula (II) is obtained according to the process described above.

The protecting group Q is for example a triphenylmethyl, tert-butyl, $C_1$–$C_4$ alkoxymethyl, methylthiomethyl, phenyl-($C_1$–$C_4$)alkoxymethyl, p-methoxybenzyl, 2,4,6-trimethylbenzyl, 1-methyl-1-phenylethyl, 2-(trimethylsilyl)ethyl, tetrahydropyranyl, piperonyl or benzenesulfonyl group.

Examples of halogenated metals represented by Z comprise —ZnCl, —MgCl, —NiCl, —CuCl, —BCl$_2$, —ZnBr, —MgBr, —CuBr, and —BBr$_2$. The synthons of formula (VI) are commercially available or can be obtained according to known methods. In any case, the preparation of a compound of formula (VI), as well as the reaction between a compound of formula (II) and a compound of formula (VI), can be carried out according to known methods, for example as disclosed in EP 579766, EP 539086, EP 760815, WO 93/10106 or EP 782996. Likewise, the removal of the protecting group Q and the optional conversion of losartan into a pharmaceutically acceptable salt can be carried out according to known methods.

The following examples illustrate the invention.

Example 1

Preparation of 1-(4-bromo-benzyl)-2-butyl-1,5-dihydroimidazol-4-one (III)

A round-bottom flask is loaded with 7.5 of 1-(4-bromobenzyl)aminoacetamide (V), 6.5 ml of trimethylorthovalerate and 0.1 ml of glacial acetic acid. The obtained biphasic mixture is placed into an oil bath at 120° C. The temperature is allowed to raise up to 105° C., thereafter the mixture is left under stirring for 1.5 h, then cooled and evaporated under high vacuum to remove all volatile substances. Compound (III) is obtained as an oil and used as such in the subsequent reaction.

Example 2

Preparation of 3-(4-bromobenzyl)-2-butyl-5-chloro-3h-imidazole-4-carboxaldehyde (IV)

1.61 g of 1-(4-bromo-benzyl)-2-butyl-1,5-dihydroimidazol-4-one and 10 ml of toluene are loaded into a round-bottom flask. The mixture is cooled down to 0–5° C., then added dropwise with 1.4 ml of phosphorous oxychloride. The temperature is slowly allowed to reach 90° C. and 1.2 ml of dimethylformamide are added dropwise. The mixture is heated at 115° C. for 2 h, then cooled to room temperature and added with 50 ml of toluene, 100 g of crushed ice and 10 g of celite. Stirring is continued for 30 minutes, then the pH is adjusted to 8 with 30% aqueous NaOH and the precipitate is filtered off using a Buchner funnel. The organic phase is concentrated under vacuum and chromatographed eluting with 1:1 v/v hexane-diethyl ether. 380 mg of product (IV) as a colourless oil is obtained.

Example 3

Preparation of 3-(4-bromobenzyl-2-butyl-5-chloro-3h-imidazol-4-yl)-methanol (II)

A round-bottom flask is loaded with 0.6 g of 3-(4-bromobenzyl)-2-butyl-5-chloro-3H-imidazole-4-carboxaldehyde and 5 ml of methanol. The mixture is cooled to 0–5° C. and added with 78 mg of sodium borohydride. Stirring is continued for 30', then 5 ml of a saturated ammonium chloride solution are added. The solvent is evaporated off and the residue is taken up with 10 ml of ethyl acetate. After two washings with 5 ml of water the organic phase is evaporated to give 480 mg of a crude residue, which is crystallized from ethanol-water. 320 mg of 3-(4-bromobenzyl-2-butyl-5-chloro-3H-imidazol-4-yl)-methanol are obtain as colourless crystals.

Example 4

Preparation of 3-(4-bromobenzyl)-2-butyl-5-chloro-3h-imidazole-4-carboxaldehyde (IV)

A round-bottom flask is loaded with 1.61 g of 1-(4-bromobenzyl)-2-butyl-1,5-dihydroimidazol-4-one, 1.80 g of N,N-dimethylformamide dimethylacetal and 10 ml of methanol; the mixture is kept under stirring at room temperature for 3 hours, then washed with 10 ml of water and the solvent is evaporated off to remove the water. The mixture is taken up with 10 ml of toluene, added dropwise with 1.4 ml of phosphorous oxychloride at 0–5° C., then gradually heated to 100° C. The reaction is continued for 2 hours, thereafter the mixture is cooled to room temperature and added with 50 ml of toluene, 100 g of crushed ice and 10 g of celite. Stirring is continued for 30 minutes, then the pH is adjusted to 8 with 30% aqueous NaOH and the precipitate is filtered off using a Buchner funnel. The organic phase is concentrated under vacuum and chromatographed eluting with 1:1 v/v hexane-diethyl ether. 360 mg of product are obtained as a colourless oil.

The invention claimed is:

1. A process for the preparation of compounds of formula (II)

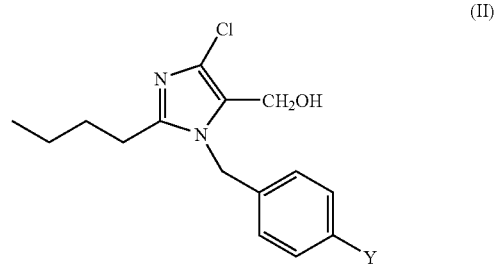

wherein Y is a leaving group, comprising:
chloroformylating a compound of formula (III)

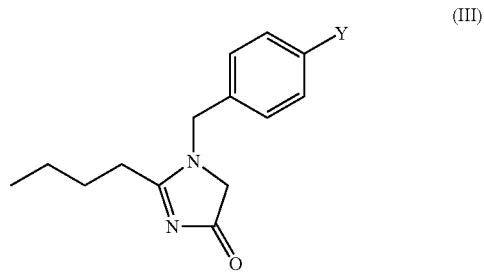

wherein Y is as defined above, to obtain a compound of formula (IV)

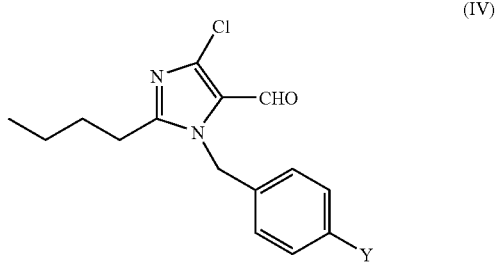

wherein Y is as defined above; and
reducing the aldehyde group to alcohol.

2. A process according to claim 1, wherein the leaving group is a halogen atom or a hydroxy group activated to esterification.

3. A process according to claim 1, wherein the chloroformylating is carried out by treatment with phosphorous oxychloride and dimethylformamide, or with a N,N-dimethylformamide dialkylacetal and phosphorous oxychloride.

4. A process according to claim 3, wherein chloroformylating is carried out in an inert organic solvent, the formylation phase is carried out at a temperature ranging from −50 to 100° C. and the chlorination phase is carried out at a temperature ranging from 50 to 150° C.

5. A process according to claim 1, wherein the reducing of the aldehyde group is carried out by treatment with an alkali metal borohydride.

6. A process according to claim 1, wherein the compound of formula (III) is obtained by reacting a compound of formula (V)

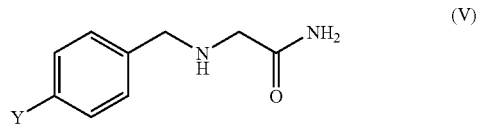

(V)

wherein Y is as defined in claim 1, with a trialkyl orthovalerate.

7. A process according to claim 6, wherein the stoichiometric ratio between a compound of formula (V) and a trialkyl orthovalerate ranges from 1/1 to 1/1.2 and the chloroformylating is carried out in the presence of a catalytic amount of an acid.

8. A process according to claim 6, wherein the compound of formula (III) is not isolated.

9. A compound of formula (III)

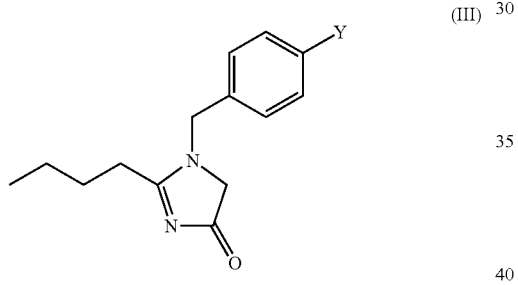

(III)

wherein Y is a leaving group.

10. The process according to claim 1, further comprising:
reacting the compound of formula (II),

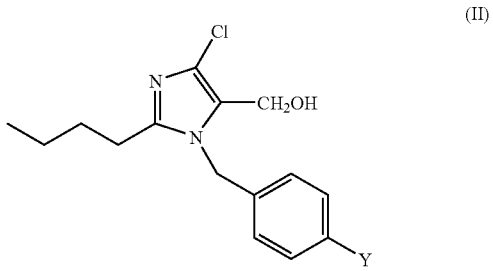

(II)

wherein Y is a leaving group,
and a synthon of formula (VI)

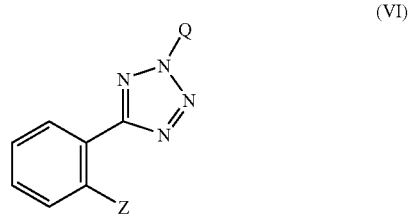

(VI)

wherein Q is a tetrazole-protecting group; and Z is a —B(R₁R₂) group wherein each of R₁ and R₂, which can be the same or different, is halogen, hydroxy or $C_1$–$C_4$ alkoxy; or Z is a lithium or copper atom, or a halogenated metal;

removing the protecting group Q; and, if desired,
converting losartan into a pharmaceutically acceptable salt thereof.

* * * * *